United States Patent [19]
Chandler

[11] Patent Number: 4,874,691
[45] Date of Patent: Oct. 17, 1989

[54] MEMBRANE-SUPPORTED IMMUNOASSAYS

[75] Inventor: Howard M. Chandler, West Vancouver, Canada

[73] Assignee: Quadra Logic Technologies Inc., Vancouver, Canada

[21] Appl. No.: 109,436

[22] Filed: Oct. 16, 1987

[51] Int. Cl.⁴ .................................. G01N 33/544
[52] U.S. Cl. .................................. 435/7; 422/58; 422/61; 422/64; 422/101; 436/518; 436/533; 436/534; 436/807; 436/535
[58] Field of Search .............. 436/518, 533, 534, 807, 436/535; 435/7; 422/61, 58, 101, 64

[56] References Cited

U.S. PATENT DOCUMENTS

| | | | |
|---|---|---|---|
| 3,832,141 | 8/1974 | Haldopoulos | 422/101 |
| 3,970,429 | 7/1976 | Updike | 436/807 X |
| 4,057,499 | 11/1977 | Buono | 422/101 X |
| 4,632,901 | 12/1986 | Valkirs | 436/548 X |

Primary Examiner—Christine M. Nucker
Attorney, Agent, or Firm—Irell & Manella

[57] ABSTRACT

Improved, economical devices for immunoassays employ a reusable syringe or vacuum manifold to withdraw samples through a membrane containing an affinity partner for analyte. The devices can also be adapted to direct blood sampling and to automated assays.

32 Claims, 5 Drawing Sheets

MEMBRANE-SUPPORTED IMMUNOASSAYS

TECHNICAL FIELD

The invention concerns the testing of samples, especially biological samples, for desired analytes using immunoassay. In particular, it concerns an improved apparatus and procedure for conducting such assays on membranes which enhance the sensitivity of the assay and the economy of the test.

BACKGROUND ART

Immunoassay procedures are so commonly used as to make unnecessary elaborate discussion of the topic in general. In is well understood that a variety of formats can be used, generally involving the conjugation of an immunoglobulin or fragment thereof to a solid support, followed by specific binding of the antigen and labeling the supported conjugate in some manner. Alternative protocols permit, for example, the antigen to be bound to the support, or the analyte to compete with its labeled counterpart. There are also immunoassays which do not involve solid supports but precipitate the immunocomplexes.

Recently, assays have been constructed wherein the immunoglobulin which is specific for analyte is embedded in a porous membrane either physically absorbed, covalently bound, or entrapped attached to particles, and this membrane is placed in contact with an absorbent material which withdraws the sample and reagent solutions through the membrane by capillary action. (See U.S. Pat. No. 4,632,901 to Hybritech). By utilizing this capillary action, the reaction time is decreased, and the assays are more convenient. The current commercial name for this format is "ICON", evidently an abbreviation of "immunoconcentration".

One disadvantage of the ICON configuration is that the use of capillary action to draw the materials through the membrane, in addition to limiting the volumes that can be used, and confining the test to individual samples, requires that the absorbent membrane and housing be discarded after each test. This increases the cost of the test, and limits sensitivity to analytes whose concentration in the test solution is sufficient to accommodate the volume requirements.

The present invention remedies these disadvantages by providing a disposable means for drawing the sample through the membrane, by providing a mechanism for utilizing arbitrary amounts of sample volume, and by providing the opportunity for simultaneous multiple sample development.

DISCLOSURE OF THE INVENTION

The invention is directed to methods and apparatus for membrane-supported immunoassay, or other specific binding assay, which permit the use of large volumes of sample, employ reusable components, and have, as the consumed component, only an inexpensive membrane assembly. The apparatus and methods of the invention also permit direct testing of blood or other withdrawn fluid samples. The method and apparatus of the invention are appropriate for any assay which is conducted on a membrane and relies on specific binding between an affinity partner and the analyte.

Thus, in one aspect, the invention is directed to a method to conduct an assay, in a (usually biological) sample, for an analyte which binds to a specific affinity partner. The specifically binding affinity partner, for example an antibody, is embedded in a membrane which is supported in an assembly which fits onto the body of a syringe or other recoverable apparatus for creating a pressure gradient. The assay is conducted by withdrawing a sample of the material to be tested through the membrane into the body of the syringe or other vacuum device. Detection and/or quantitation of the analyte from the sample bound to the membrane is then achieved by conventional means, such as binding to additional specific affinity partners which contain label. The preferred methods of the invention may include washing steps which can also be conducted by withdrawing the wash solution through the membrane.

In another aspect, the invention relates to various improved designs for apparatus useful in the method of the invention. One such design comprises the membrane supported in a syringe-compatible assembly. Another design provides a disposable membrane support which can be placed on a flat surface and maintains the horizontal position of the membrane as well as providing means for linking to a syringe or to another vacuum device. Still other designs include removable chambers which permit placement of reagents on top of the membrane prior to application of a vacuum, and additional upstream components which permit packaged supply of reagents or direct sampling of body fluids. A variety of designs is compatible with the method of the invention.

In still another aspect, the invention is directed to test kits suitable for conducting these methods.

BRIEF DESCRIPTION OF THE DRAWINGS

FIGS. 3A and 3B shows an improved design for a membrane supporting member which provides stable disposition of the membrane.

MODES OF CARRYING OUT THE INVENTION

Figure 2:
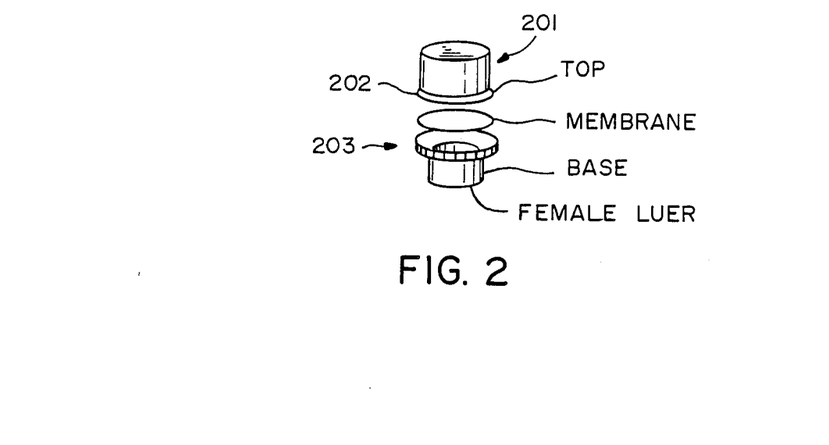
FIG. 2 shows an embodiment of the invention assembly components.
Figure 3A:
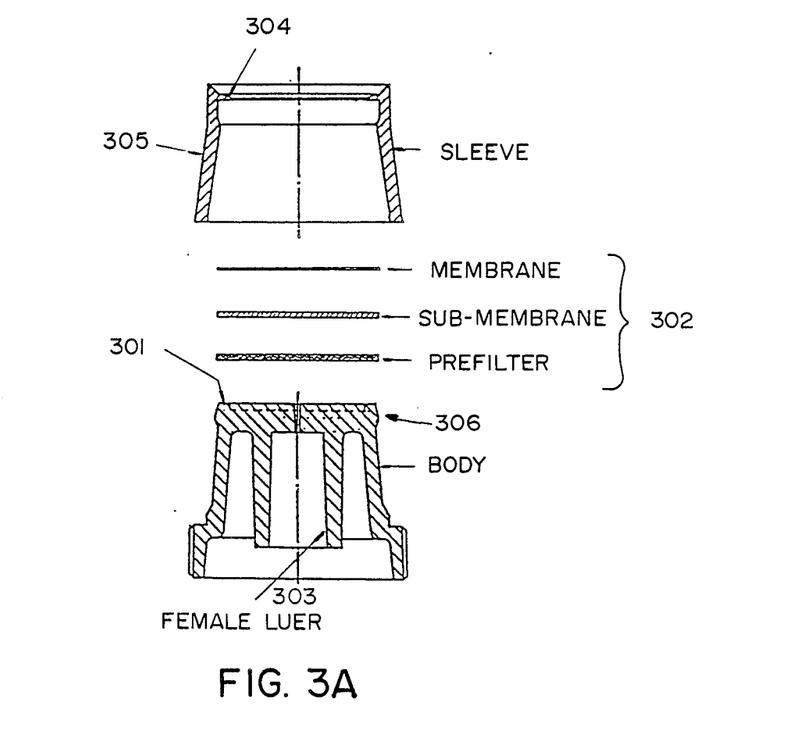

The invention employs a membrane assembly typified but not limited by the embodiments shown as separate components in FIGS. 2 and 3. In these preferred embodiments, a membrane, which can be constructed of conventional materials used in immunoassay procedures, such as cellulose acetate, fiberglass, nitrocellulose, nylon and the like is supported in a simple assembly which is designed to stand alone and/or to interface with the body of a syringe or other device for creating a pressure gradient. The supporting assembly can be composed of one or more simple injection-molded components.

The "chemistry" of the assays is drawn from standard immunoassays and similar specific binding assays, generally known in the art. The most commonly used tests are immunometric assays in which the membrane contains an antibody or a fragment thereof, such as an Fab or F(ab')$_2$ fragment specific for the analyte to be detected or measured. The binding of the analyte to the membrane depends on the specificity of this antibody. The bound analyte is then detected by a variety of strategies as outlined below.

Numerous commonly known assays are based on antigen-antibody interactions, and both polyclonal and monoclonal antibody preparations are used to effect the desired specific interaction. Of course, the method of the invention is not limited to this, most common, specific binding format. Specific binding also occurs, for example, between hormones and receptors, lectins and glycosylated proteins, and avidin and biotin. The method, apparatus, and kits of the invention are applicable to any assay which relies on the specific capture of the analyte in the membrane by virtue of an interaction with a reagent embedded therein. The reagent must simply bind analyte to the exclusion of other substances present in the test sample.

Conventionally, the retention of the analyte in the membrane is detected by use of still another specific reagent which binds to the membrane only when analyte is present, and in proportion to the amount of analyte retained. Typically, this is an additional antibody or other specifically binding preparation which contains some form of labeling such as radioisotopes, fluorescent materials, or an enzyme. Typical labels include iodine-131, P-32, or other radioisotopes linked to the labeling reagent, for example, for antibodies, through protein A, fluorescent materials such as fluorescein or dansyl, enzymes which catalyze reactions which can be detected by a change in color, such as alkaline phosphatase or horseradish peroxidase, or other label such as colloidal gold. If the enzyme based label is used, a substrate solution needs also to be added in order to develop the detectable result.

The foregoing protocols are typical, but, of course, alternative procedures still consistent with the method of the invention are also contemplated. For example, a labeled conjugate may be initially embedded in the membrane, and the analyte binding may alter the conformation of the conjugate in such a way as to activate an enzyme used as label. In this case, no additional labeled conjugate need be added, but only the substrate solution.

In addition, the analyte may itself be an antibody, and the antigen or hapten used to entrap it in the membrane. Any affinity-pairing partner to the analyte is used in construction of the reactive membrane. As used herein "affinity partner" refers to any substance which binds to the analyte. In most protocols, the affinity partner included in the membrane will be "specific" to the analyte —— i.e., it will bind to analyte to the exclusion of other components of the specimen which would otherwise interfere with the test. However, this need not be the case; the specificity could also be confined by the labeling reagent.

The assembly of the invention, which is inexpensively made and disposable, is adapted for use with a replaceable and detachable means for applying a pressure gradient across the membrane. This means can be as simple as an ordinary syringe or can be a specially designed vacuum manifold.

By avoiding the use of capillary action (as described in U.S. Pat. No. 4,632,901) for withdrawal of the sample and reagent through the membrane, not only can an expensive portion of the test assembly (the absorbent pad) can be replaced by a reusable component, but the test can be adapted to protocols that permit more flexibility in the manner of conducting the test. In particular:

(1) Because the pressure gradient can now be applied at will, several tests can be run simultaneously; control specimens can thus be included and the quantitative aspects of the test improved.

(2) Because the sample is withdrawn in volume across the membrane, it can be made to carry with it additional reagents, preferably supplied on an upstream porous support.

(3) Because the pressure gradient car be supplied by syringe, a blood sample, for example, car be withdrawn and passed directly through the membrane.

The foregoing modifications to the conventional method and the specially designed apparatus for performing them are included in the invention.

The Membrane Supporting Member

There are a number of workable designs for a membrane supporting means which are compatible with use in the methods of the invention. Preferred embodiments are shown in FIGS. 2 and 3.

The support housing of FIG. 2 contains two interlocking members. The top member as shown in FIG. 2 is a cylinder 201, providing an inlet through which the sample will be drawn, with a flange 202 at the bottom. The membrane is then placed against the flange and secured by the base, which contains a complementary flange clamping member 203. The base is thus secured to the flange with the membrane sealed so as to prevent leakage of fluids around the membrane. The base further comprises a female Luer lock for late assembly onto a syringe.

The housing for the membrane shown in FIG. 3 is also in two parts. The membrane 302 is seated on the bottom member 301, which in this illustration contains a female Luer opening 303 for a syringe. The membrane is held in place by the projection 304 from the outer housing 305. The outer housing is held in place by virtue of the design of the lip at the top 306, assembled upside down.

In use for both designs, the membrane is placed on the base and the top is secured thereto as shown. Preferably, the entire assembly is provided as a disposable unit rather than assembled at the site of the assay. As the components are quite inexpensive, the use of pre-assembled units is practical, and provides a more reproducible and easily achieved result.

Figure 1:
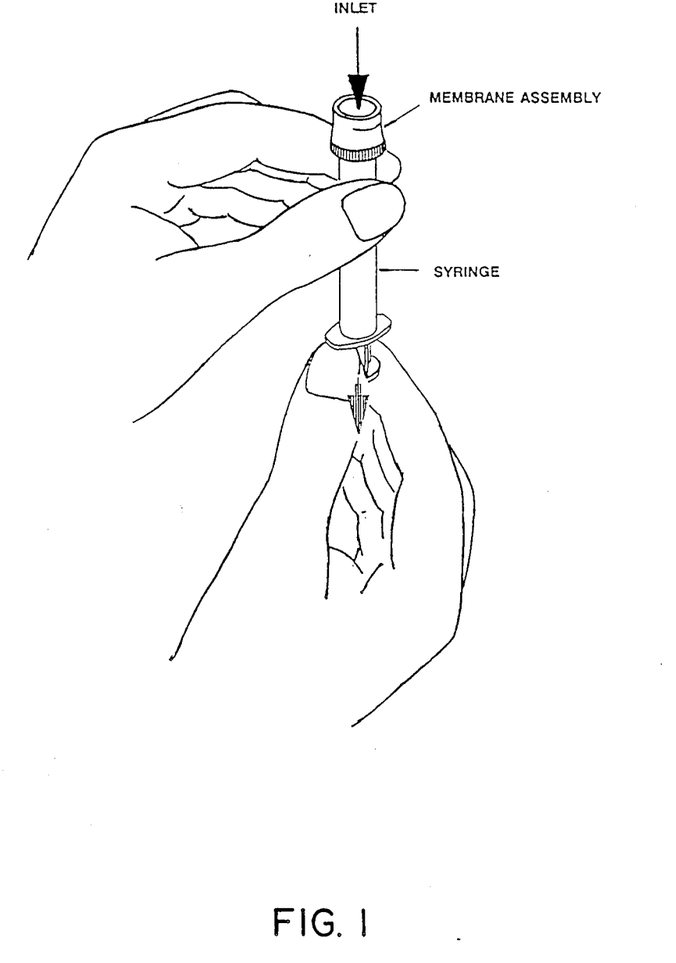
FIG. 1 shows an embodiment of an apparatus of the invention assembled in, position at the syringe inlet.

FIG. 1 shows the assembled support of FIG. 2 attached to a conventional syringe. This attachment is made through the Luer lock, and commercially available syringes are suitable. The housing shown in FIG. 3 may be similarly attached.

Figures 4, 5:
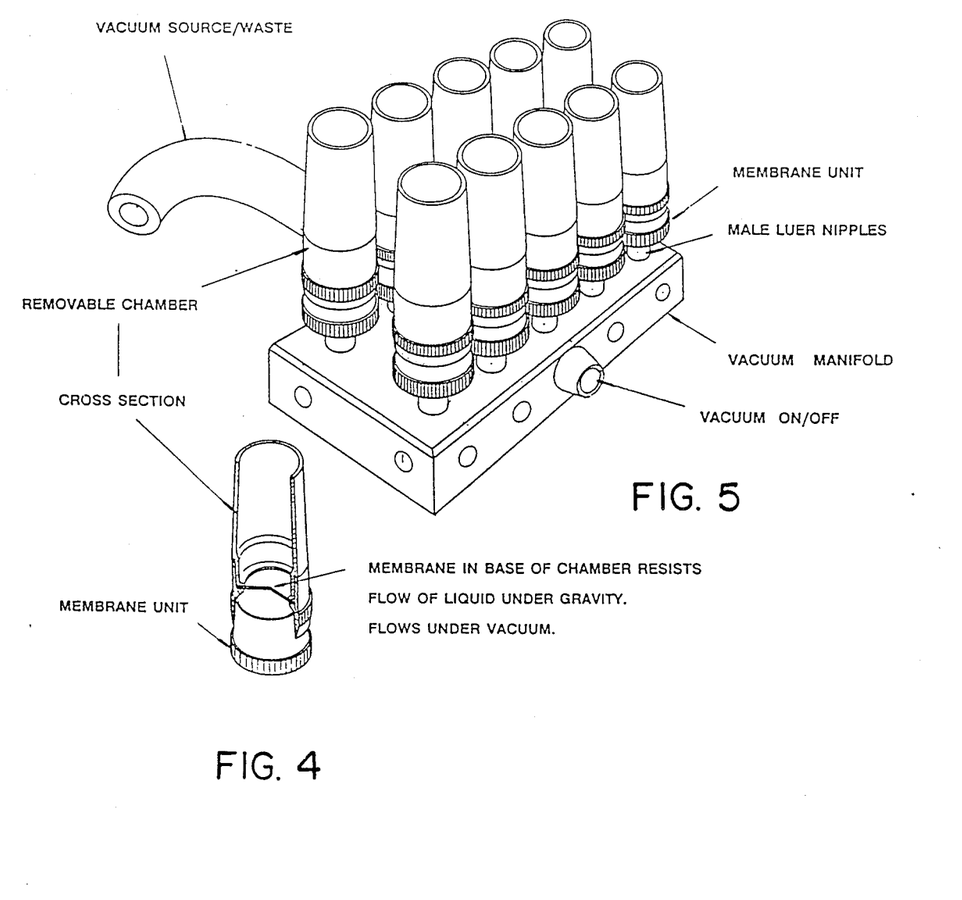
FIG. 4 shows disposition of the membrane housing with a removable chamber.
FIG. 5 shows a conceptual drawing of a vacuum manifold to which the membrane housings can be attached.

Other design modifications can also be used to adapt the assay to particular conditions. For example, as shown in FIG. 4, the housing can be fitted with a removable chamber which holds reagents or samples which are "waiting" to be drawn through the membrane. This is useful in a number of circumstances, but in particular if multiple samples are to be compared or simply assayed at one time. In this case, the vacuum manifold shown in FIG. 5 will also be useful. The membrane units are placed on the manifold as shown in the diagram using for example, male Luer nipples and the sample or reagent is allowed to sit on top of the membrane without application of the pressure differential until the desired number of manifold positions is filled (gravity will be insufficient to withdraw the sample through the membrane) Any unfilled positions are then stoppered and the vacuum is turned on so that the membranes are simultaneously impregnated with the sample material. Thus, standardization of contact time and simultaneous reaction are assured, and all tests will receive the same time of exposure to both the specimen and reagent. An additional advantage of the multiplicity of samples is that control specimens can be used to permit visual estimation of color intensity of development of unknowns. This results in a semi-quantitative assay.

In a typical procedure to conduct the method of the invention, an antibody specific to the analyte to be detected has been absorbed in the membrane of the assembly. The assembly is then attached to the body of a syringe of appropriate volume, typically 5-25 ml. The volume of the syringe should preferably exceed the volume of the sample, as it can then accommodate both sample and wash solutions.

The appropriate sample volume is then withdrawn into the syringe and through the membrane. Of course, the use of the syringe provides an automatic measurement of the volume used; typical sample volumes are of the order of 5-10 ml, but a wider range of volumes is usable, according to the choice of syringe. As stated above, the syringe should be chosen so that the volume will also accommodate wash solutions; for example, if a 5 ml sample volume is needed, a 10 ml syringe is appropriate.

After the sample is withdrawn through the membrane into the syringe, the membrane may optionally be washed with, for example, 2-3 ml of water, but this is not necessary.

The detecting conjugate or reagent is then added to the membrane. This can be done by adding drops of detecting solution directly to the membrane, or a small volume may be withdrawn from a diluted solution of conjugate or reagent through the membrane into the syringe. The detection reagent is allowed to remain in contact with the membrane for a preset time, usually of the order of 1 or 2 minutes, or even less, before washing. Washing is done by withdrawing an additional sample of water through the membrane into the syringe.

If the product of the detecting solution, such as of conjugate containing label, is detectable per se, the results of the test are read directly. If not, for example, if an enzyme-mediated test is used, a substrate solution is added to the membrane either by withdrawal through the membrane of a dilute solution of substrate or by adding drops. Incubation of the substrate solution with the membrane for an appropriate time, again approximately 1-2 minutes, permits the development of the detectable result.

Generally speaking, the tests on sample are run in conjunction with positive and negative controls wherein the same procedure is used, but substituting a solution containing a known amount of analyte as a positive control or from which analyte is absent for a negative control.

Multiple Simultaneous Samples

An alternative procedure is particularly useful when controls are to be run, and thus multiple samples required. In this approach, the membrane holders or housings, such as those typified in FIGS. 2 or 3 are placed onto the openings, for example, Luer nipples, of a manifold. In multiple samples, it is advantageous also to utilize the removable chambers, since the membranes need to be impregnated with sample and reagent simultaneously. Thus, at the start, the membrane housings containing these chambers are placed on the manifold.

The required volumes of specimens or controls are added to each chamber and the vacuum is turned on and maintained until all specimens have passed into the manifold. The vacuum is then released and the next reagent, typically a labelled conjugate, is added to each chamber. Vacuum is then applied again, and a suitable reaction time is permitted before washing with distilled water or wash solution by addition of solution to each chamber and application and release of vacuum.

If enzyme label is used, the substrate reagents are then applied to the chambers and withdrawn into the membrane by application and release of the vacuum, and allowed to react for a suitable time, typically 0.5-5 min. The samples may then be washed again if necessary, and the results read directly, typically after removal of the chambers by suitable densitometer or other comparative methods.

Packaged Upstream Reagents

Figure 6:
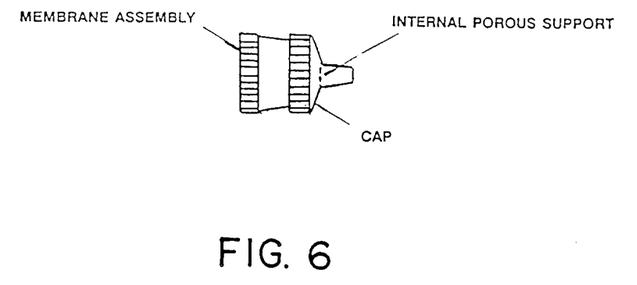
FIG. 6 shows a cap arrangement for a premeasured conjugate to be reacted with sample.

In still another alternative, the membrane format can be applied in connection with a porous support upstream of the membrane in the flow of specimen, which contains the labeling reagent or conjugate and thus prereacts with the analyte in the specimen before entrapment in the membrane. This porous support can be placed in the removable chamber for the application to manifold vacuum withdrawal or can be placed upstream of the membrane in a syringe arrangement by means of an external cap preceding the housing membrane. A suitable arrangement is diagrammed in FIG. 6, where the membrane assembly, such as that of FIG. 3, is fitted with the cap containing the porous support.

In one typical embodiment, the porous support contains labelled conjugate antibody directed to an analyte to be tested. The sample is drawn through the porous support and the analyte thus carries the label with it past the membrane. As before, the analyte, now bound to label, is also concentrated on the membrane. The cap is then removed for reading, if the label is read directly, or if enzyme label is used the substrate solution is added. In the case of the manifold the substrate is added directly to the outer chamber; if the syringe assembly is used, withdrawn through the membrane. Reading of the results is done conventionally.

This alternative reduces the procedure to two steps and simplifies the procedure, although a small increment of cost is thus added to the test by virtue of the necessity to construct the porous support. The workability of this alternative also relies on the stability of the labeling reagent in the porous support.

Direct Sample Measurement

Figure 7:
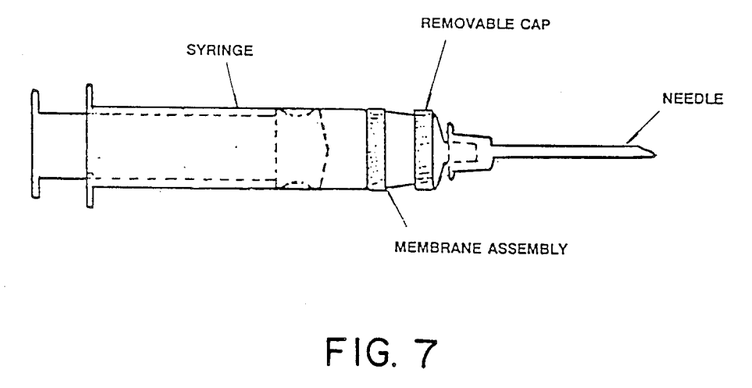
FIG. 7 shows an apparatus for direct measurement of blood.

In addition, the apparatus can be modified to obtain and measure a sample of blood or other internal fluids which are generally removed through hypodermic needles directly. Rather than supply of the sample in a container or chamber, blood for example, is withdrawn directly through the membrane and then the remainder of the assay procedure conducted as described above. A suitable apparatus for this approach is shown in FIG. 7 wherein the membrane assembly depicted in FIG. 3 is fitted with a cap containing the male Luer nipple for a syringe needle. The sample is thus withdrawn directly past the membrane and into the syringe in a manner similar described above, except that the sample is not separately collected in the chamber.

Membrane-Bound and Upstream Porous Support-Bound Reagent

Conjugate or other reagents may be freeze-dried while on the support to increase stability. Thus the membranes or other supports may be prepared to include reagent in a variety of procedures, but advantageously, the last step in such procedures is the freeze-drying of the materials while in contact with the support. Solutions or suspensions of the reagents are placed in contact with the supporting materials and dried either under ambient pressure or reduced pressure, including lyophilization. In the alternative, the reagents can be placed on beads, such as latex beads, and these solid carriers embedded in the support materials. Suitable membrane or support materials include nylon, cellulose, nitrocellulose, fiberglass, or other fibers.

Kits

It is convenient for the invention method to be packaged as a kit. A typical kit would contain one or more of the membrane assemblies with reagents appropriate for use in a particular assay in suitable containers for easy use. In certain embodiments, the disposable outer chambers, caps, and porous supports or caps and needles will also be supplied.

The syringe or vacuum manifold is reusable; typically, a kit would contain a single syringe or manifold and a plurality of membrane assemblies and other accessories with sufficient reagent to run the appropriate number of assays. Replacement kits need not include the syringe or manifold.

The kit may also include materials and apparatus which render the test easier to do, such as a rack for placement of the syringe and dropping bottles for dispensing the reagents, as well as tissues, disposable pipettes, and other optional items of convenience. Generally, however, the kits will contain instructions for performance of the test. The instructions should be quite straightforward, and indeed, as the kits are particularly intended for regions where technology is not advanced, the instructions will be detailed, and amply illustrated.

Automation

Any of the devices and designs of the invention can be adapted to an automated process for conducting the assay. This is convenient for clinical laboratories or for any location where large numbers of tests are run. The membrane unit, for example, that of FIG. 2, could be used in a fully automated instrument shown diagramatically in FIG. 8.

Figure 8:
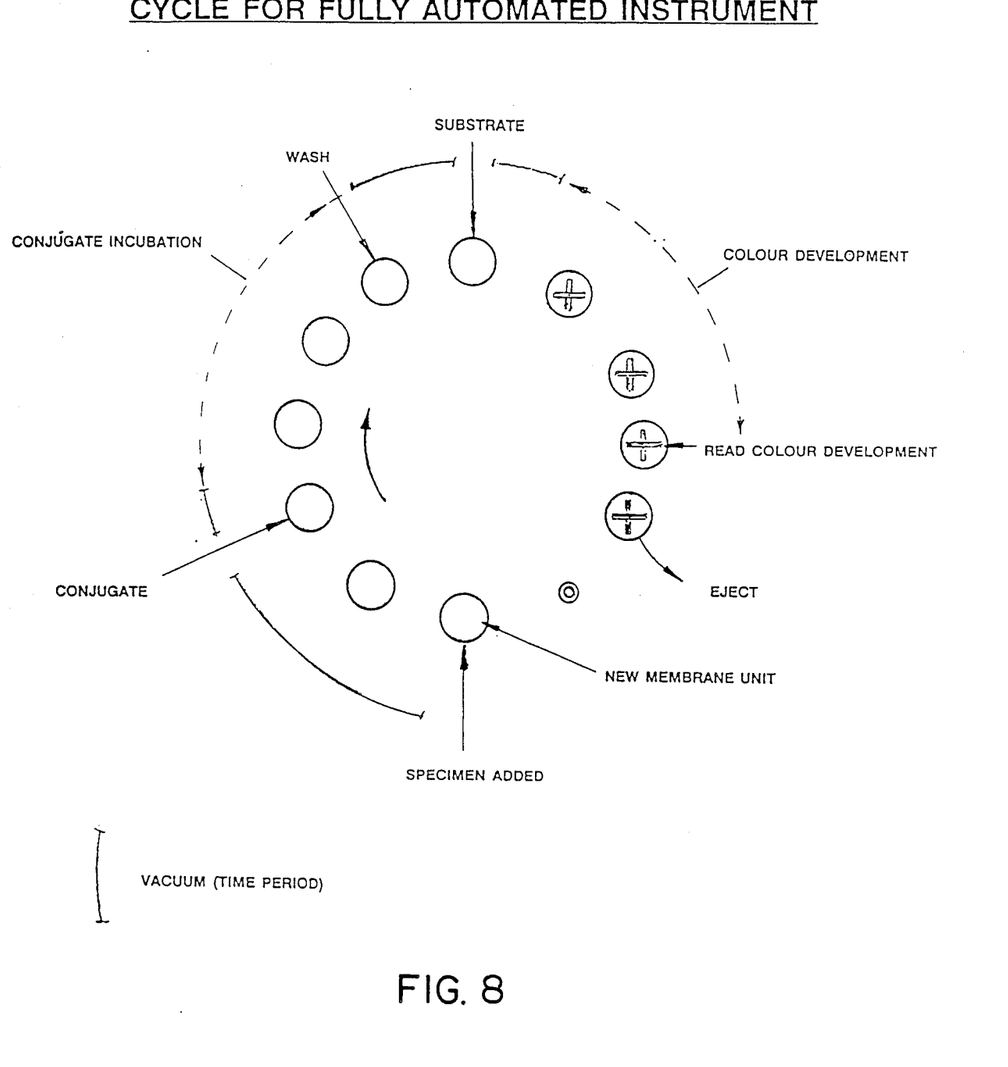
FIG. 8 shows a schematic of an adaptation of the membrane assembly to automated assay.

In this schematic, the membrane assembly would replace the test tubes used currently in a number of automated RIA and EIA systems. Membrane assembly units would be fitted (automatically if necessary) to vacuum nipples on a turntable or conveyor belt and specimen added. The unit would then advance to a point where vacuum would be applied to draw the specimen through the membrane into the waste chamber of the instrument. The unit would next pass under a dispensing head where conjugate would be added and at the next point it would be drawn through the membrane to waste. Typically the unit would then advance to receive wash and substrate if required. The membrane would then pass under a reflectance spectrophotometer where the color development would be read and, by reference to values obtained with control specimens, a quantitative result calculated. Finally the membrane unit would be ejected to waste and the cycle completed as the nipple advanced to receive another membrane unit.

By this means testing could proceed continuously at a rate controlled only by the capacity of the instrument. Even a very small instrument with 12 nipples on a 3 minute test cycle (as used for hCG) could complete 240 tests per hour.

The following procedure is intended to illustrate, but, of course, not to limit the invention.

EXAMPLE 1

Determination of Human Chorionic Gonadotropic (HCG) in Urine

The membrane assembly contains anti-HCG, prepared by impregnating the membrane with 1 ul of 1-5 mg/ml solution of the monoclonal antibody. The membrane unit is fitted to a 10 ml syringe and the inlet cylinder contacted to a urine specimen in a conventional container. A 5 ml sample of the specimen is drawn through the membrane into the syringe. HCG present in the sample is retained by binding the anti-HCG in the membrane.

The syringe is placed in a support to permit the membrane to retain a horizontal position at the top of the syringe. To the membrane is then added three drops of conjugate reagent. The conjugate reagent contains 40 $\mu$g/ml anti-HCG antibody, conjugated to alkaline phosphatase in PBS buffer, pH 7.2. (Conjugation of the alkaline phosphatase to anti-CG is conducted by standard procedures as described by Avrameas, S., et al, *Scand J. Immunol* (1978) 8, Suppl 7: 7-23, and results in a concentration of enzyme per antibody of 1:1 on a molar basis.)

The membrane is then let stand for 1 minute, and 2 ml of distilled water are then drawn through the membrane into the syringe.

To the membrane is then added 3 drops of substrate solution containing indoxyl phosphate 37 $\mu$M, in 0.1 M buffer, pH 9.5. The substrate is then incubated for 1 minute, and the intensity of blue color developed is a measure of the HCG present in the sample. Positive and negative controls are treated similarly using a standard solution containing 50 mIU/ml of HCG and a blank containing no HCG.

The amount of HCG is estimated by comparison to the standard solution result, or by comparison to standard color charts.

EXAMPLE 2

Preparation of Anti-HCG Membrane

A. Direct

Membranes may be obtained in chemically activated form from several commercial suppliers, e.g. Pall or Millipore.

Typically, 1 $\mu$l of a 1-5 mg/ml antibody solution in phosphate buffered saline (PBS) is spotted directly onto the membrane and left at room temperature for 1 minute. The remaining active sites on the membrane are then blocked by incubation with 0.1% casein in PBS for 15 minutes at room temperature. The coated membrane may then be stored moist (e.g. in PBS containing 0.1% sodium azide) or dried and stored dry.

B. Indirect

Latex particles are coated with antibody (either by passive adsorption or covalent attachment) and then physically entrapped within an inert membrane support, as follows: Seragen TM amino-modified latex was incubated with 1% glutaraldehyde in distilled water for 2 hours at room temperature and then washed with PBS. Antibody in PBS (1 mg) was added to the latex particles overnight at 4° C. The particles were then washed with PBS and finally made to a 1% suspension with PBS.

Ten $\mu$l of the antibody-coated latex suspension was spotted onto a low protein binding membrane (0.45 micron, Millipore), and all non-specific binding sites on the membrane blocked by storing the membranes until used in a 0.1% solution of casein in PBS containing 0.1% sodium azide. If required the membranes may be dried and stored dry.

I claim:

1. A method to conduct an assay for an analyte in a sample, wherein the analyte binds to an affinity partner, which method comprises:
   drawing a volume of said sample by means of a pressure gradient through a membrane in which the affinity partner for the analyte is contained into a receiving chamber on which said membrane is mounted,
   wherein said pressure gradient is obtained by creating a partial vacuum in said receiving chamber, and
   detecting the analyte bound in the membrane.

2. The method of claim 1 wherein the receiving chamber is the body of a syringe.

3. The method of claim 1 wherein the receiving chamber is a vacuum manifold.

4. The method of claim 1 wherein the affinity partner for the analyte is a specific affinity partner.

5. The method of claim 1 wherein the affinity partner for the analyte is an immunoglobulin or derivative thereof.

6. The method of claim 1 wherein the affinity partner for the analyte is an antigen or hapten.

7. The method of claim 1 wherein the bound analyte is detected by reaction with a labeled immunoglobulin or derivative thereof.

8. The method of claim 7 wherein the immunoglobulin or derivative thereof is an antibody specific for the analyte.

9. The method of claim 8 wherein the labeled antibody is labeled with an enzyme.

10. The method of claim 2 wherein the sample is blood or internal body fluids drawn directly past the membrane.

11. A method to conduct an assay for analyte in two or more samples simultaneously wherein the analyte binds to an affinity partner, which method comprises:
    placing a volume of each sample in contact with one of a multiplicity of membranes in each of which the affinity partner for the analyte is contained,
    wherein each of said multiplicity of said membranes is mounted onto a common receiving chamber, and
    in a single operation withdrawing each sample by means of a pressure gradient applied as a partial vacuum in said receiving chamber through the membrane into said receiving chamber, and
    detecting the analyte bound in each membrane from each sample.

12. The method of claim 11 wherein each sample is placed in an outer chamber affixed to the corresponding membrane and wherein said pressure gradient is obtained by creating a partial vacuum in said receiving chamber.

13. An apparatus for the detection of analyte in a sample wherein the detection comprises reaction of said analyte with an affinity partner, which apparatus comprises:
    a supported membrane containing said affinity partner, wherein said membrane is supported at the upper portion of a housing wherein said housing further includes means to attach said membrane to an orifice of a receiving chamber in which a partial vacuum can be created.

14. The apparatus of claim 13 which further includes the body of a syringe attached to the housing.

15. The apparatus of claim 13 wherein the affinity partner is a specific affinity partner.

16. The apparatus of claim 13 wherein the affinity partner is an immunoglobulin or derivative thereof.

17. The apparatus of claim 13 wherein the affinity partner is an antigen or hapten.

18. The apparatus of claim 16 wherein the immunoglobulin or derivative thereof is an antibody specific for the analyte.

19. The apparatus of claim 13 wherein the housing supports the membrane in a horizontal position.

20. The apparatus of claim 13 wherein said housing engages said membrane by means of a deformable lip.

21. The apparatus of claim 13 wherein the membrane is engaged at the top face of the housing.

22. The apparatus of claim 13 which further includes an outer chamber disposed at the top of the housing capable of accommodating the sample.

23. The apparatus of claim 13 wherein said apparatus comprises an upper portion and a lower portion,
    wherein said lower portion is a luer socket contiguous with a lip portion and
    wherein said upper portion is a cylindrical chamber having at one end a flange of dimension to engage said lip of the lower portion and
    wherein said membrane is supported between the flange of the upper portion and lip of the lower portion.

24. The apparatus of claim 13 wherein said apparatus has an upper portion and a lower portion,
    wherein said lower portion is a luer socket having at one end an extended rim on which said membrane is supported,
    said upper portion fitting annularly at the exterior surface of the lower portion and having at the top thereof a lip extension which engages the membrane supported on the lower portion.

25. The apparatus of claim 22 wherein said apparatus has a top portion and bottom portion,
    wherein said top portion is a cylindrical chamber containing at its base said membrane,
    said cylindrical chamber having an engaging means adjacent said membrane for attachment of said top portion to said bottom portion,
    wherein said bottom portion contains an engaging means for the top portion and a means for attachment of the apparatus to a vacuum manifold.

26. A method to conduct an assay for analyte in a sample, wherein the analyte binds to a first affinity partner and wherein said binding is detected by reaction with a labeled second affinity partner, wherein at least one of said first and second affinity partners is specific for analyte, which method comprises:

drawing a volume of said sample by means of a pressure gradient through a porous support containing said labeled second affinity partner and through a membrane in which the first affinity partner is contained into a receiving chamber, wherein said pressure gradient is obtained by creating a partial vacuum in said receiving chamber.

27. An apparatus for conducting an assay for analyte in a sample which comprises: a needle; attached to a housing in which is supported a membrane containing an affinity partner for the analyte, which membrane is connected to a receiving chamber which includes a means of applying a pressure gradient through the needle and past the membrane into the chamber.

28. An apparatus for conducting an assay for an analyte in a sample which comprises a means for applying a pressure gradient past a membrane in which a first affinity partner for the analyte is contained, into a receiving chamber and having upstream of said membrane a porous support containing a second affinity partner conjugated to label, wherein at least one of said first and second affinity partners is specific for analyte.

29. A kit suitable for conducting measurement of an analyte in a biological sample which reagent kit comprises:

the supported membrane unit of claim 13, reagents in separate bottles, and instructions for conducting the assay.

30. The kit of claim 29 which further includes a syringe

31. The kit of claim 29 which further includes a vacuum manifold.

32. The kit of claim 30 wherein the syringe is reusable.

* * * * *